United States Patent
Zhu

(10) Patent No.: US 10,819,703 B2
(45) Date of Patent: Oct. 27, 2020

(54) DEVICE AND METHOD FOR AUTHENTICATION

(71) Applicant: BOE TECHNOLOGY GROUP CO., LTD., Beijing (CN)

(72) Inventor: Lin Zhu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 210 days.

(21) Appl. No.: 16/023,064

(22) Filed: Jun. 29, 2018

(65) Prior Publication Data
US 2019/0058703 A1    Feb. 21, 2019

(30) Foreign Application Priority Data
Aug. 18, 2017 (CN) .......................... 2017 1 0711838

(51) Int. Cl.
*H04L 29/06* (2006.01)
*H04L 29/08* (2006.01)
(Continued)

(52) U.S. Cl.
CPC ............ *H04L 63/083* (2013.01); *A61B 5/048* (2013.01); *A61B 5/04842* (2013.01);
(Continued)

(58) Field of Classification Search
CPC ... H04L 63/083; H04L 63/0861; H04L 67/10; H04L 67/02; H04L 63/08; A61B 5/048;
(Continued)

(56) References Cited

U.S. PATENT DOCUMENTS 4,279,258 A * 7/1981 John .................. A61B 5/04014
                                                  600/544
9,047,604 B2 * 6/2015 Herder ............... G06Q 20/3674
(Continued)

FOREIGN PATENT DOCUMENTS

| CN | 103310142 A | 9/2013 |
| CN | 106137187 A | 11/2016 |
| CN | 106778186 A | 5/2017 |

OTHER PUBLICATIONS

First Office Action for Chinese Patent Application No. 201710711838.5 dated Oct. 23, 2019.

*Primary Examiner* — David J Pearson
*Assistant Examiner* — Badri Champakesan
(74) *Attorney, Agent, or Firm* — Calfee, Halter & Griswold LLP

(57) ABSTRACT

A device and method for user authentication. The device for authentication includes an extraction unit configured to extract a signal feature of a brainwave signal of a user to be authenticated and a comparison unit configured to compare the signal feature with a signal feature sample pre-stored in a feature library on an individual basis. When there a signal feature sample is matched with the signal feature, the device retrieves account information and a password of the user according to the matched signal feature sample. The device for authentication further includes a response unit configured to respond to a request of the user according to the account information and the password. The present disclosure can improve the security and convenience of user authentication.

18 Claims, 10 Drawing Sheets

(51) Int. Cl.
    *A61B 5/00*     (2006.01)
    *A61B 5/117*     (2016.01)
    *G06F 21/31*     (2013.01)
    *A61B 5/0484*     (2006.01)
    *G06F 21/32*     (2013.01)
    *A61B 5/048*     (2006.01)

(52) U.S. Cl.
    CPC .......... *A61B 5/04845* (2013.01); *A61B 5/117* (2013.01); *A61B 5/7267* (2013.01); *G06F 21/316* (2013.01); *G06F 21/32* (2013.01); *H04L 63/0861* (2013.01); *H04L 67/10* (2013.01)

(58) Field of Classification Search
    CPC . A61B 5/04845; A61B 5/04842; A61B 5/117; A61B 5/7267; G06F 21/32; G06F 21/316
    USPC .......................................................... 726/7
    See application file for complete search history.

(56) References Cited

U.S. PATENT DOCUMENTS

| | | | |
|---|---|---|---|
| 9,268,905 B2* | 2/2016 | Garripoli | A61B 5/048 |
| 9,326,086 B2* | 4/2016 | Tsang | H04R 29/00 |
| 9,432,361 B2* | 8/2016 | Mahaffey | H04W 12/003 |
| 9,579,035 B2* | 2/2017 | Sarkela | G06K 9/00523 |
| 9,672,760 B1* | 6/2017 | Breuer | H04L 9/3247 |
| 10,341,339 B2* | 7/2019 | Laine | A61B 5/01 |
| 2009/0063866 A1* | 3/2009 | Navratil | A61B 5/0484 |
| | | | 713/186 |
| 2009/0150919 A1* | 6/2009 | Lee | H04N 21/235 |
| | | | 725/10 |
| 2009/0318826 A1* | 12/2009 | Green | A61B 5/04014 |
| | | | 600/545 |
| 2014/0230018 A1* | 8/2014 | Anantharaman | H04L 63/0861 |
| | | | 726/4 |
| 2014/0325646 A1* | 10/2014 | Turgeman | H04L 63/08 |
| | | | 726/22 |
| 2015/0238122 A1 | 8/2015 | Navratil et al. | |
| 2015/0338917 A1* | 11/2015 | Steiner | H04M 1/7253 |
| | | | 345/156 |
| 2016/0004862 A1* | 1/2016 | Almehmadi | G06F 21/6218 |
| | | | 726/25 |
| 2017/0164878 A1* | 6/2017 | Connor | A61B 5/4866 |
| 2017/0188933 A1* | 7/2017 | Huggins | A61B 5/7435 |
| 2017/0312476 A1* | 11/2017 | Woo | A61M 21/02 |
| 2018/0285540 A1* | 10/2018 | Chen | G06F 21/32 |

\* cited by examiner

DEVICE AND METHOD FOR AUTHENTICATION

RELATED APPLICATION

The present application claims the benefit of Chinese Patent Application No. 201710711838.5, filed on Aug. 18, 2017, the entire disclosure of which is incorporated herein by reference.

FIELD

The present disclosure relates to the technical field of intelligent hardware, and more particularly to a device and method for authentication.

BACKGROUND

With the rapid development of technologies, cloud services have been increasingly applied. For example, cloud desktop is a typical application in the cloud computing era. Cloud desktops can provide data space and management services to users in the form of desktops, which are suitable to be used as network operating systems for mini hand-held mobile applications such as tablets and mobile phones, and can also upgrade the traditional personal computers (PCs) to network operation. Thus, cloud desktop is a very convenient office service for users who often have to be out of office or on business trips. However, users only rely on account information and login password for logging in a cloud desktop, which results in poor security and inconvenient information input.

SUMMARY

Thus, according to a first embodiment of the present invention, there is provided a device for authentication, comprising: an extraction unit configured to extract a signal feature of a brainwave signal of a user to be authenticated; a comparison unit configured to compare the signal feature with signal feature sample pre-stored in a feature library on an individual basis, and when there is a signal feature sample matched with the signal feature, retrieve account information and a password of the user according to the matched signal feature sample; and a response unit configured to respond to a request of the user according to the account information and the password.

In certain exemplary embodiments, the response unit comprises a sending unit and a receiving unit. The sending unit is configured to send a cloud desktop login request to a cloud server, the cloud desktop login request comprising the account information and the login password. The receiving unit is configured to receive a cloud desktop returned by the cloud server in response to the cloud desktop login request.

In certain exemplary embodiments, the device for authentication further comprises a feature library unit and an association unit. The feature library unit is configured to determine a signal feature sample corresponding to a specific thinking activity for the user by learning the signal feature of the brainwave signal generated by the user when he/she conducts the specific thinking activity. The association unit is configured to associate the determined signal feature sample with the account information and the password of the user so as to generate an item in the feature library.

In certain exemplary embodiments, the specific thinking activity comprises a thinking activity when the user is receiving a specific audiovisual content, and/or a thinking activity when the user is having a specific imagination.

In certain exemplary embodiments, the feature library unit is configured to determine a plurality of corresponding sub-signal feature samples for a plurality of specific thinking activities of the user respectively. The association unit is configured to generate an item in the feature library for each of the plurality of determined sub-signal feature samples respectively.

In certain exemplary embodiments, the feature library unit comprises: a first decomposition unit configured to decompose the brainwave signal generated by the user into multiple first sub-waveforms and extract from them a first sub-waveform that has a frequency within a predetermined frequency range; a first computation unit configured to compute a first amplitude difference, which is the amplitude difference between the extracted first sub-waveform and a predetermined reference waveform; and a first determination unit configured to, when the first amplitude difference is within a first predetermined amplitude difference range, determine the frequency of the extracted first sub-waveform and the first amplitude difference as the signal feature sample corresponding to the user.

In certain exemplary embodiments, the extraction unit comprises: a second decomposition unit configured to obtain the brainwave signal of a user to be authenticated, decompose the brainwave signal of the user to be authenticated into multiple second sub-waveforms, and extract from them a second sub-waveform that has a frequency within a predetermined frequency range; a second computation unit configured to compute a second amplitude difference, which is the amplitude difference between the extracted second sub-waveform and a predetermined reference waveform; and a second determination unit configured to, when the second amplitude difference is within a second predetermined amplitude difference range, determine the frequency of the extracted second sub-waveform and the second amplitude difference as the signal feature of the user to be authenticated.

In certain exemplary embodiments, the comparison unit is further configured to compare the signal feature with signal feature sample pre-stored in a feature library on an individual basis by: computing the similarity between the signal feature of the user to be authenticated and the signal feature sample so as to determine whether the similarity reaches a similarity threshold.

In certain exemplary embodiments, the comparison unit is further configured to compute the similarity according to a ratio of the number of feature elements identical to those of the signal feature of the user to be authenticated to the total number of feature elements in the signal feature sample.

In certain exemplary embodiments, the device for authentication further comprises an execution unit, being configured to generate an instruction for controlling an application according to the signal feature of the brainwave signal of the user.

In certain exemplary embodiments, the instruction for controlling an application comprise at least one selected from a group consist of: a page switch instruction, a file switch instruction, a play forward instruction, a play backward instruction, a file sharing instruction, and a location sharing instruction.

According to a second embodiment of the present invention, there is provided a method for authentication. The method comprises: extracting a signal feature of a brainwave signal of a user to be authenticated; comparing the signal feature with a signal feature sample pre-stored in a feature library on an individual basis, and, when there is a signal feature sample matched with the signal feature, retrieving account information and a password of the user according to the matched signal feature sample; and responding to a request of the user according to the account information and the password.

In certain exemplary embodiments, the password comprises a login password. The responding to the request of the user according to the account information and the password comprises: sending a cloud desktop login request to a cloud server, the cloud desktop login request comprising the account information and the login password; and receiving a cloud desktop returned by the cloud server in response to the cloud desktop login request.

In certain exemplary embodiments, before extracting a signal feature of a brainwave signal of a user to be authenticated, the method further comprises: determining a signal feature sample corresponding to a specific thinking activity for the user by learning the signal feature of the brainwave signal generated by the user when he/she conducts the specific thinking activity; and associating the determined signal feature sample with the account information and the password of the user so as to generate an item in the feature library.

In certain exemplary embodiments, the specific thinking activity comprises a thinking activity when the user is receiving a specific audiovisual content, and/or a thinking activity when the user is having a specific imagination.

In certain exemplary embodiments, determining the signal feature sample corresponding to a specific thinking activity for the user comprises: determining a plurality of corresponding sub-signal feature samples for a plurality of specific thinking activities of the user respectively; and said generating an item in the feature library comprises: generating an item in the feature library for each of the plurality of determined sub-signal feature samples respectively.

In certain exemplary embodiments, the determining the signal feature sample corresponding to the user comprises: decomposing the brainwave signal generated by the user into multiple first sub-waveforms and extracting from them a first sub-waveform that has a frequency within a predetermined frequency range; computing a first amplitude difference, which is the amplitude difference between the extracted first sub-waveform and a predetermined reference waveform; and when the first amplitude difference is within a first predetermined amplitude difference range, determining the frequency of the extracted first sub-waveform and the first amplitude difference as the signal feature sample corresponding to the user.

In certain exemplary embodiments, the extracting a signal feature of a brainwave signal of a user to be authenticated comprises: obtaining the brainwave signal of the user to be authenticated, decomposing the brainwave signal of the user to be authenticated into multiple second sub-waveforms, and extracting from them a second sub-waveform that has a frequency within a predetermined frequency range; computing a second amplitude difference, which is the amplitude difference between the extracted second sub-waveform and a predetermined reference waveform; and determining the frequency of the extracted second sub-waveform and the second amplitude difference as the signal feature of the user to be authenticated when the second amplitude difference is within a second predetermined amplitude difference range.

According to a third embodiment of the present invention, there is provided a computer program product comprising a computer readable storage medium storing instructions, that, when executed, enable at least one central processor unit of the computing device to carry out the method according to the second embodiment of the disclosure.

According to a fourth embodiment of the present invention, there is provided a system for authentication, comprising one or more processors and a memory coupled to the one or more processors, the memory comprises instructions, that, when executed by the one or more processors, enable the system to carry out the method according to the second embodiment of the disclosure.

DETAILED DESCRIPTION

For the purpose of making the objects, technical solutions and advantages of the present disclosure more apparent, the present disclosure will be further noted in detail in view of the embodiments and with reference to the drawings.

Unless otherwise defined, the technical terms or scientific terms used herein shall have the ordinary meanings that can be understood by those skilled in the art. "First", "second" and similar words used herein do not indicate any order, quantity or importance, but are used to distinguish different components. Likewise, such words as "a", "an" or "the" do not indicate a limitation in quantity, but mean at least one. Such words as "comprise" or "include" indicate that an element or component before such words cover the elements, components and equivalents thereof listed thereafter, and do not exclude the presence of other elements or components. Such words as "connect" or "couple" do not only refer to a physical or mechanical connection, but may include an electrical connection, either directly or indirectly.

With the development of Human-Computer Interaction (HCI) technology, relevant HCI technologies have gradually developed towards intelligent interaction, natural interaction etc. The focus of HCI changes from defining interaction manners, designing interaction semantics, etc. to, e.g., paying attention to users' brainwaves for further digging their hidden requirements.

A brainwave is formed by summarization of postsynaptic potentials occurring simultaneously in a large number of neurons when a brain is active. It records the changes of electrical waves of an active brain, and is a general reflection of the electrophysiological activity of brain nerve cells on the cerebral cortex or scalp surface. Hence, a brainwave is an important biological feature signal, characterizing activities of human brains.

Figure 1:
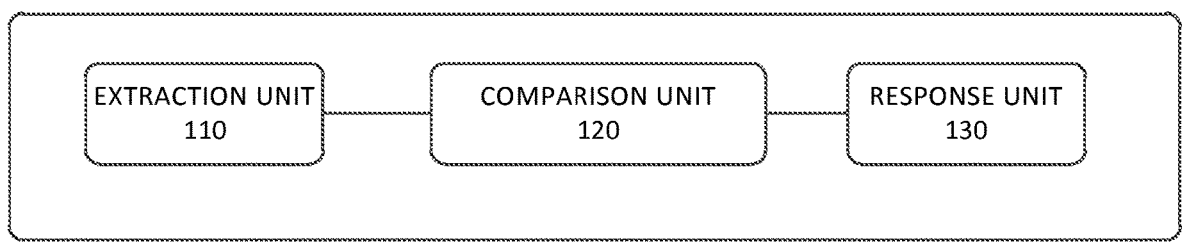
FIG. 1 illustrates an exemplary block diagram of an authentication device according to an embodiment of the present disclosure.

FIG. 1 illustrates an exemplary block diagram of an authentication device according to an embodiment of the present disclosure. As an embodiment of the present disclosure, an authentication device 100 comprises an extraction unit 110, a comparison unit 120 and a response unit 130. The extraction unit 110 is configured to extract a signal feature of a brainwave signal of a user to be authenticated. The comparison unit 120 is configured to compare the signal feature with a signal feature sample(s) pre-stored in a feature library, and, when there is a signal feature sample matched with the signal feature, retrieve account information and a password of the user according to the matched signal feature sample. The response unit 130 is configured to respond to a request of the user according to the account information and the password.

The authentication device provided by embodiments of the present disclosure may authenticate based on the user's brainwave signal feature, which improves the security and convenience of identity authentication for the user. Once the identity of the user is authenticated, the authentication device may respond to the request of the user, thereby further improving user experience.

It should be noted that the request of the user to be authenticated may be, but not limited to, a login request, a payment request, a deletion request, a revocation request or an amendment request. Correspondingly, the password may be, but not limited to, a login password, a payment password, a deletion password, a revocation password or an amendment password. The login request may be, but not limited to, a request for logging into a user account on a browser (e.g., a request for logging in a cloud desktop) or a request for logging into a user account on an application.

Figure 2:
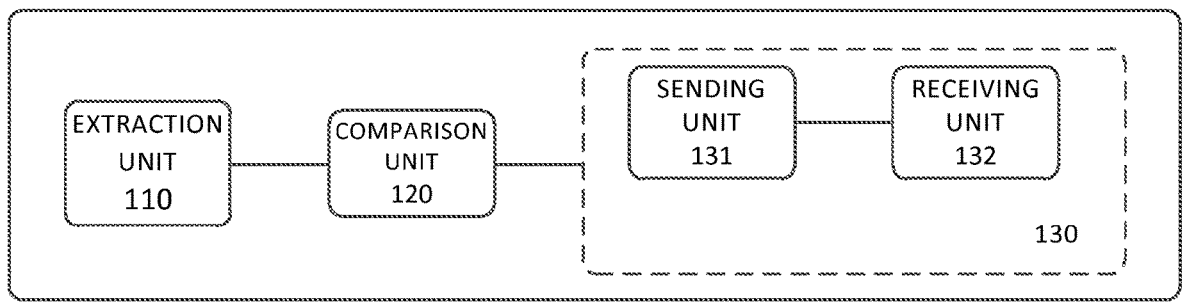
FIG. 2 illustrates an exemplary block diagram of an authentication device according to another embodiment of the present disclosure.

FIG. 2 illustrates an exemplary block diagram of an authentication device according to another embodiment of the present disclosure. As an embodiment of the present disclosure, an authentication device 100 comprises an extraction unit 110, a comparison unit 120 and a response unit 130. The response unit 130 comprises a sending unit 131 and a receiving unit 132. In the embodiment, the extraction unit 110 is configured to extract a signal feature of a brainwave signal of a user to be authenticated. The comparison unit 120 is configured to compare the signal feature with a signal feature sample(s) pre-stored in a feature library so as to determine whether there is a signal feature sample matched with the signal feature. If there is a matched signal feature sample, account information and a login password of the user to be authenticated may be retrieved according to the matched signal feature sample. The sending unit 131 is configured to send a cloud desktop login request to a cloud server, which comprises the account information and the login password. The receiving unit 132 is configured to receive a cloud desktop returned by the cloud server in response to the cloud desktop login request.

The authentication device provided by embodiments of the present disclosure may authenticate a user identity according to the user's brainwave signal feature. Once the authentication is passed, it is possible to directly send a cloud desktop login request to a cloud server and then log into the cloud desktop, which may improve the security and convenience of logging into a cloud desktop.

The authentication device in the embodiments may be specifically implemented as a terminal, such as a cloud terminal, a PC, a hand-held device (e.g., a mobile phone or tablet) or a wearable device (e.g., a wrist band or head-mounted display device).

It shall be noted that the brainwave signal of a user may be collected by a brainwave detection device, such as a brainwave electrode cap. The brainwave detection device may communicate with the authentication device 100 e.g., in a wired or wireless manner, so as to transmit the collected brainwave signal to the authentication device 100. The wireless communication manners may include, but not limited to, the communication using an infrared technology or Bluetooth technology. The authentication device 100 implements user identity authentication based on the brainwave signal by means of the extraction unit 110, the comparison unit 120, the sending unit 131 and the receiving unit 132.

In comparison with other manners of authentication in relevant technologies, including a manner of biological feature authentication, authentication with brainwave is more accurate. Moreover, brainwave signal features are characterized by hardness to replicate and uniqueness, which guarantees the security and accuracy of logging into a cloud desktop.

Brainwave waveforms are mainly classified according to their frequencies. In general, a waveform having a lower frequency has higher amplitude, and a waveform having a higher frequency has lower amplitude. Brainwave signals may be mainly divided into the following types: $\delta$ wave having a frequency range of 1-3 Hz and an amplitude of 20-200 $\mu$V; $\theta$ wave having a frequency range of 4-7 Hz and an amplitude of 5-20 $\mu$V; $\alpha$ wave having a frequency range of 8-13 Hz (a mean value of 10 Hz) and an amplitude of 20-100 $\mu$V; and $\beta$ wave having a frequency range of 14-30 Hz and an amplitude of 100-150 $\mu$V.

In some embodiments, signal feature samples may be stored in a memory. The memory, for example, may comprise a volatile memory and/or a non-volatile memory, and, for example, may comprise multiple types of storage devices or storage media such as a read-only memory (ROM), a hard disk, a flash memory. The signal feature samples may be operated by a specialized processing unit or a general processing unit, e.g., by the comparison unit 120.

Figure 3:
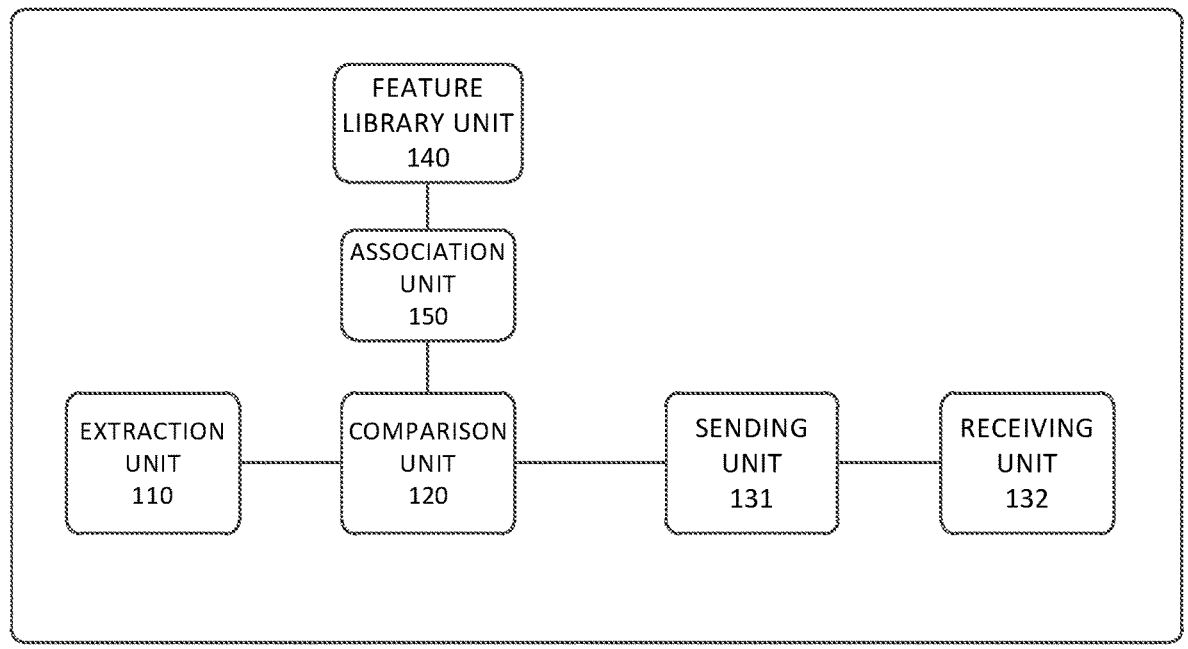
FIG. 3 illustrates an exemplary block diagram of an authentication device according to another embodiment of the present disclosure.

FIG. 3 illustrates an exemplary block diagram of an authentication device according to another embodiment of the present disclosure. As an embodiment of the present disclosure, an authentication device 100 comprises an extraction unit 110, a comparison unit 120, a sending unit 131, a receiving unit 132, a feature library unit 140 and an association unit 150. The feature library unit 140 is configured to learn the signal feature of the brainwave signal generated by a user when he/she conducts a specific thinking activity, and determine a signal feature sample of the user corresponding to the specific thinking activity. The association unit 150 is configured to associate the determined signal feature sample with account information and a password(s) of the user so as to generate an item in the feature library. For example, the item may comprise the determined signal feature sample and the account information as well as the password(s), or association or link between determined signal feature sample and the account information as well as the password(s). The feature library unit 140 and the association unit 150 determine signal feature samples corresponding to different users by respectively learning the various thinking activities of the different users multiple times. It should be noted that accuracy of the signal feature samples may be improved by increasing learning times. The signal feature sample of each user is associated with the account information and the password of the user in a one-to-one relationship. Thus, the user's identity may be accurately determined by his/her brainwave signal, thereby guaranteeing the security and accuracy of logging into the cloud desktop.

In some embodiments of the present disclosure, in order to further improve the authentication security and accuracy, the signal feature sample of each user may comprise a plurality of sub-signal feature samples, and each sub-signal feature sample corresponds to a signal feature of a category of specific thinking activities. For example, categories of specific thinking activities may comprise an audiovisual category of thinking activities when a user is receiving a specific audiovisual content, and/or an imaginary category of thinking activities when a user is having a specific imagination. For instance, an audio file or a video file may be played to a user, and the user's brainwave signal collected at this time may be learned so as to determine the signal feature sample corresponding to the user. In certain exemplary embodiments, the audio file may be rock music or lullaby, and the video file may be a dancing video, a game video or a teaching video. For instance, it is also possible to show a word or a color to a user, and the user's brainwave signal collected at this time may be learned so as to determine the signal feature sample corresponding to the user. In certain exemplary embodiments, the word may be sun or running water, etc., and the color may be red or black, etc. For instance, it is also possible to require a user to imagine an action, and the user's brainwave signal collected at this time may be learned so as to determine the signal feature sample corresponding to the user. In certain exemplary embodiments, the action may be running, sword dancing or sleeping, etc. For example, it is also possible to require a user to image a task or a physical object, and the user's brainwave signal collected at this time may be learned so as to determine the signal feature sample corresponding to the user. In certain exemplary embodiments, the task may be word recitation, and the physical object may be a football. Thus, after learning multiple times, it is possible to obtain the signal feature sample comprising a plurality of sub-signal feature samples corresponding to different thinking activities of a user. Therefore, in comparison with the authentication through static biological features, such as a fingerprint or an iris, the identity authentication has better accuracy, diversity and flexibility.

In some embodiments, the feature library unit 140 may be configured to determine a plurality of corresponding sub-signal feature samples for a plurality of specific thinking activities of a user respectively. For example, the feature library unit 140 may determine a first sub-signal feature sample when a first image is shown to the user, and determine a second sub-signal feature sample when a second image is shown to the user. The association unit 150 may be configured to associate the determined first and second sub-signal feature samples respectively with different or same account information or password(s) so as to generate a first item and a second item. The first and second items may be added to the feature library.

Figure 4:
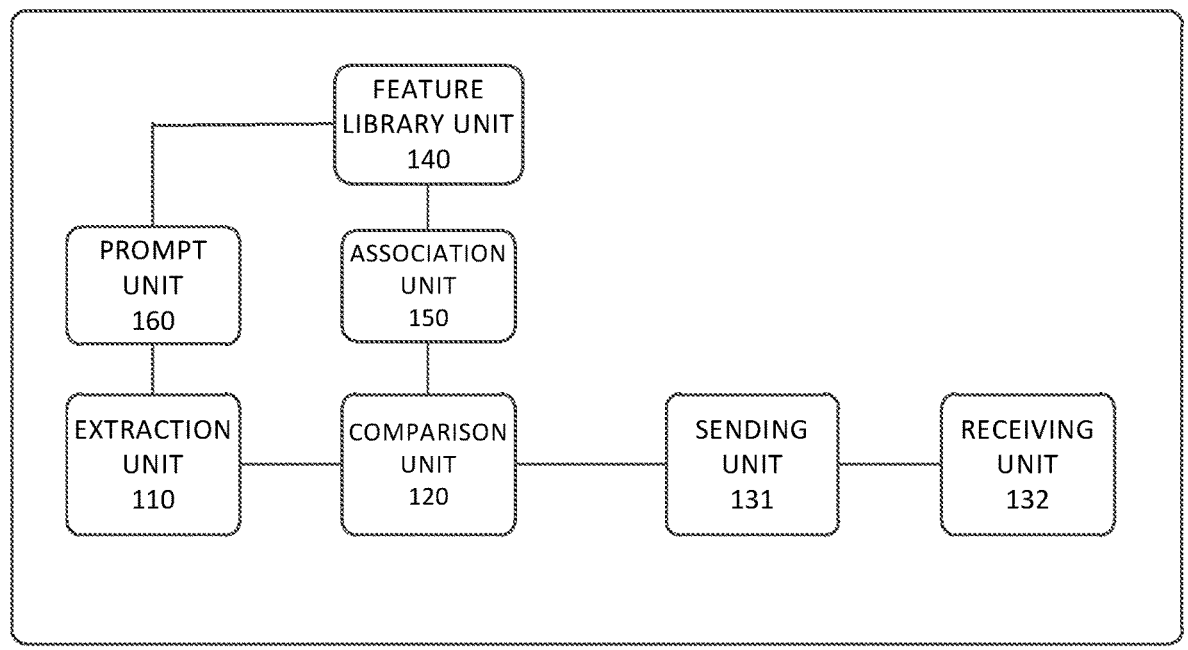
FIG. 4 illustrates an exemplary block diagram of an authentication device according to a further embodiment of the present disclosure.

Correspondingly, FIG. 4 illustrates an exemplary block diagram of an authentication device according to a further embodiment of the present disclosure. As shown in FIG. 4, the authentication device 100 further comprises a prompt unit 160. The prompt unit 160 is configured to prompt unit 160 category information corresponding to the signal feature sample when a brainwave detection device collects the brainwave signal of a user. The category information may indicate a corresponding thinking activity a user is required to conduct. For example, category information for prompt may be: please imagine you are running, or please imagine you are reciting a word, etc. The prompt unit 160 may also be configured to prompt category information when the feature library unit 140 is learning the signal feature of the brainwave signal generated by the user. The feature library unit 140 determines the signal feature sample corresponding to the category information. It shall be noted that the category information prompted by the prompt unit 160 may be identical to the corresponding category information when the feature library unit 140 determines the signal feature sample. The comparison unit 120 may compare the signal feature with the signal feature samples pre-stored in the feature library on the basis of the same category of features, so as to improve the accuracy of identity authentication.

As an embodiment of the present disclosure, the prompt unit 160 is configured to prompt at least one of various categories of information corresponding to the signal feature sample when the brainwave detection device is collecting the user's brainwave signal. As yet another embodiment of the present disclosure, the prompt unit 160 is configured to prompt two or more of various categories of information corresponding to the signal feature sample when the brainwave detection device is collecting the user's brainwave signal. For example, an audio file is played first to the user, and the user's brainwave signal collected at this time is learned to determine a sub-signal feature sample corresponding to the user. Then, a color is shown to the user, and the user's brainwave signal collected at this time is learned to determine another sub-signal feature sample corresponding to the user. Later, the user is required to imagine an action, and the user's brainwave signal collected at this time is learned to determine still another sub-signal feature sample corresponding to the user. The comparison unit 120 is configured to compare a signal feature corresponding to category information prompted by the prompt unit 160 with the sub-signal feature sample corresponding to the category information pre-stored in the feature library one by one.

Figure 5:
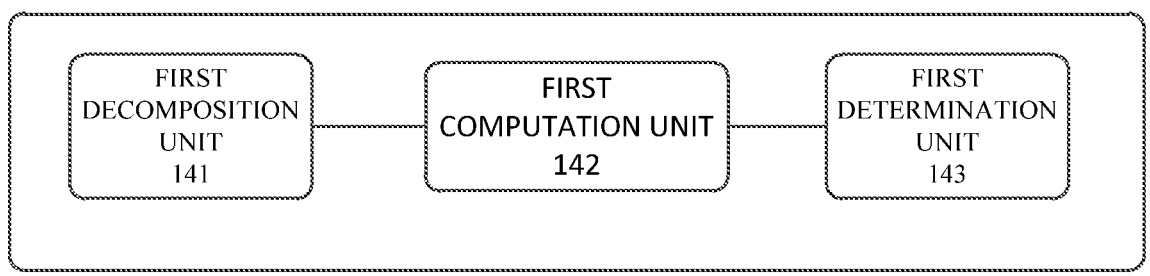
FIG. 5 illustrates an exemplary block diagram of a feature library unit according to an embodiment of the present disclosure.

FIG. 5 illustrates an exemplary block diagram of a feature library unit according to an embodiment of the present disclosure. As a further embodiment of the present disclosure, as shown in FIG. 5, the feature library unit 140 comprises: a first decomposition unit 141, a first computation unit 142 and a first determination unit 143. In the embodiment, the first decomposition unit 141 is configured to decompose the brainwave signal generated by a user into multiple first sub-waveforms, from which a first sub-waveform that has the frequency within a predetermined frequency range is extracted. The first computation unit 142 is configured to compute a first amplitude difference, which is the amplitude difference between the extracted first sub-waveform and a predetermined reference waveform. The first determination unit 143 is configured to determine whether the first amplitude difference is within a first predetermined amplitude difference range. If yes, the frequency of the extracted first sub-waveform together with the first amplitude difference may be determined as a signal feature sample corresponding to the user. In this way, the feature library unit 140 obtains the signal feature sample by decomposing the brainwave signal into multiple first sub-waveforms and computing the amplitude differences between the first sub-waveforms and the reference waveform, so as to authenticate the user's identity based on the signal feature sample during the authentication.

As an embodiment of the present disclosure, the brainwave signal generated by a user may be decomposed into N (N being a natural number larger than zero) sections of first waveforms according to different time periods, and then M (M being a natural number larger than zero) sections of second waveforms are selected from the N sections. In such a way, the brainwave signal generated by the user is decomposed into multiple first sub-waveforms. In this embodiment, the comparison and analyses are performed by applying a section-by-section comparison mode.

As an embodiment of the present disclosure, the brainwave signal generated by a user may be decomposed into N (N being a natural number larger than zero) sections of first waveforms according to different time periods, and then a portion of each of M sections of first waveforms out of the N sections is taken according to a certain step-size to form second waveforms, In such a way, the brainwave signal generated by the user is decomposed into multiple first sub-waveform. In this embodiment, the comparison and analyses are performed by applying a step-size based mode.

The first determination unit 143 obtains signal feature samples for the user's brainwave signal at different time instances according to whether the first amplitude difference is within the first predetermined amplitude difference range. The signal feature sample is a matrix-type signal feature $Im=[\phi(ti), f]$, wherein $\phi(ti)$ represents the amplitude difference between the user's brainwave signal and the reference waveform at the time ti, and f represents the frequency of the user's brainwave signal. Thus, the matrix comprises a plurality of feature elements with each representing the frequency of the user's brainwave signal at the time ti and the amplitude difference between the user's brainwave signal and the reference waveform at the time ti.

A reference waveform may be a waveform composed of $\alpha$, $\beta$, $\theta$, $\delta$ frequencies, wherein the waveform peaks of respective frequencies are respectively in the normal range. It should be noted that the predetermined reference waveform may be a reference waveform self-defined by the user, so as to compute the amplitude difference with reference to it. As an example, a predetermined reference waveform may be:

$$I_{ref} = \begin{cases} [\phi_\alpha(ti), f_\alpha], & (20 < \phi_\alpha < 100 \ uV, \quad 8 < f_\alpha < 13) \\ [\phi_\beta(ti), f_\beta], & (5 < \phi_\beta < 22 \ uV, \quad 14 < f_\beta < 30) \\ [\phi_\theta(ti), f_\theta], & (20 < \phi_\theta < 150 \ uV, \quad 4 < f_\theta < 7) \\ [\phi_\delta(ti), f_\delta], & (20 < \phi_\delta < 200 \ uV, \quad 0.5 < f_\delta < 3) \end{cases}.$$

As another embodiment of the present disclosure, the first decomposition unit 141 is configured to pre-process the brainwave signal generated by the user to obtain a first analog waveform. Then, the first analog waveform is decomposed into multiple analog sub-waveforms, from which an analog sub-waveform that has a frequency within a predetermined frequency range is extracted. Correspondingly, in the embodiment, a first amplitude difference is an amplitude difference between the extracted analog sub-waveform and the predetermined reference waveform. By pre-processing the brainwave signal generated by the user and using the pre-processed analog waveform as a comparison object, the regularity of the brainwave waveform is improved, thereby enhancing the working efficiency of the first determination unit 143 so that it may efficiently obtain effective signal feature samples. In certain exemplary embodiments, the pre-processing may comprise, but not limited to the processing such as denoising and amplification, thereby obtaining an analog waveform that facilitates subsequent information processing.

Figure 6:
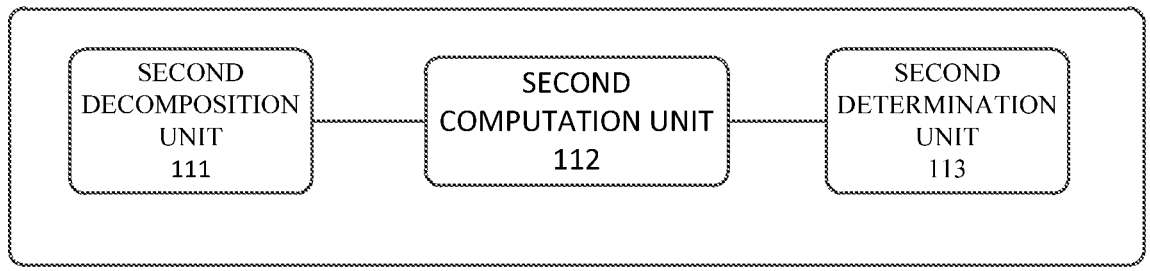
FIG. 6 illustrates an exemplary block diagram of an extraction unit according to another embodiment of the present disclosure.

FIG. 6 illustrates an exemplary block diagram of an extraction unit according to another embodiment of the present disclosure. As another embodiment of the present disclosure, the extraction unit 110 comprises a second decomposition unit 111, a second computation unit 112 and a second determination unit 113. The second decomposition unit 111 is configured to obtain a brainwave signal of a user to be authenticated and decompose the brainwave signal of the user to be authenticated into multiple sections of second sub-waveforms, from which a second sub-waveform that has a frequency within a predetermined frequency range is extracted. The second computation unit 112 is configured to compute a second amplitude difference. The second amplitude difference is the amplitude difference between the extracted second sub-waveform and the predetermined reference waveform. The second determination unit 113 is configured to determine whether the second amplitude difference is to within a second predetermined amplitude difference range. If yes, the frequency of the extracted second sub-waveform together with the second amplitude difference may be determined as the signal feature of the user. In this way, the extraction unit 110 obtains the signal feature of the user to be authenticated by decomposing the brainwave signal into multiple sections of second sub-waveforms and computing the amplitude differences between the multiple sections of second sub-waveforms and the reference waveform, so as to compare the signal feature of the user with a signal feature sample for authenticating the user's identity.

As an embodiment of the present disclosure, the brainwave signal of the user to be authenticated may be decomposed into R (R being a natural number larger than zero) sections of first waveforms according to different time periods, and then S (S being a natural number larger than zero) sections of second waveforms are selected from the R sections. In such a way, the brainwave signal of the user to be authenticated is decomposed into multiple sections of second sub-waveforms. It should be pointed out that R may be identical to or different from N. S may be identical to or different from M. The second predetermined amplitude may be identical to or different from the first predetermined amplitude. In this embodiment, the comparison and analyses are performed by applying a section-by-section comparison mode.

As another embodiment of the present disclosure, the brainwave signal generated by a user may be decomposed into R (R being a natural number larger than zero) sections of first waveforms according to different time periods, and then out of the R sections, a portion of each of S sections of first waveforms is taken according to a certain step-size to form second waveforms, In such a way, the brainwave signal generated by the user is decomposed into multiple second sub-waveforms. In this embodiment, the comparison and analyses are performed by applying a step-size based mode.

The second determination unit 113 obtains signal features of the brainwave signal of the user to be authenticated at different time instances according to whether the second amplitude difference is within the second predetermined amplitude difference range. The signal feature is a matrix-type signal feature $Pm=[\phi(ti), f]$, $i=1, 2, 3 \ldots$, wherein $\phi(ti)$ represents the amplitude difference between the user's brainwave signal and the reference waveform at the time ti, and f represents the frequency of the user's brainwave signal. Thus, the matrix comprises a plurality of feature elements with each representing the frequency of the brainwave signal of the user to be authenticated at certain time and the amplitude difference between the brainwave signal of the user to be authenticated and the reference waveform at certain time.

As a further embodiment of the present disclosure, the second decomposition unit 111 is configured to pre-process the brainwave signal of the user to be authenticated to obtain a second analog waveform, and then decompose the second analog waveform into multiple analog sub-waveforms, from which an analog sub-waveform that has a frequency within a predetermined frequency range is extracted. Correspondingly, in the embodiment, the second amplitude difference is an amplitude difference between the extracted analog sub-waveform and the predetermined reference waveform. By pre-processing the brainwave signal of the user to be authenticated and using the pre-processed analog waveform as a comparison object, the regularity of the brainwave waveform is improved, thereby enhancing the working efficiency of the second determination unit 113 so that it may efficiently obtain effective signal features. In certain exemplary embodiments, the pre-processing may comprise, but not limited to the processing such as denoising and amplification, thereby obtaining an analog waveform that facilitates subsequent information processing.

As a yet embodiment of the present disclosure, the comparison unit 120 is configured to compute the similarity between the signal feature of the user to be authenticated and a signal feature sample pre-stored in the feature library so as to determine whether their similarity reaches a similarity threshold; and if the similarity reaches the similarity threshold, the account information and the password of the user may be extracted through the matched information feature sample. In the embodiment, the similarity threshold may be pre-determined, such as 80%, 85% or 90%. When the similarity between the signal feature of a user to be authenticated and the signal feature sample pre-stored in the feature library exceeds the similarity threshold, it is deemed that they match with each other.

To be specific, the comparison unit 120 is configured to compare a signal feature $Pm=[\phi(ti), f]$ of the user to be authenticated with a signal feature sample $Im=[\phi(ti), f]$ pre-stored in the feature library on a feature element-by-feature element basis, so as to determine whether corresponding feature elements in the two matrixes are the same. A method for computing the similarity is to compute the number of feature elements identical to those of the signal feature of the user to be authenticated divided by the total number of feature elements in the signal feature sample. In certain exemplary embodiments, the signal feature $Pm=[\phi(ti), f]$ is compared with the signal feature sample $Im=[\phi(ti), f]$ pre-stored in the feature library on a parameter-by-parameter basis according to positions of the parameters in the matrices so as to improve the accuracy of comparison. It should be noted that there are many ways to determine whether a pair of feature elements are the same. For example, this may be done by comparing the amplitude difference between feature elements. If the amplitude difference between the two feature elements is within a certain range, it may be determined that they are the same, though the present disclosure is not limited thereto.

As a further embodiment of the present disclosure, the comparison unit 120 is configured to compute the similarity between the signal feature of the user to be authenticated under some category information and the signal feature sample corresponding to the category information so as to determine whether the similarity reaches a predetermined similarity. If the similarity reaches the predetermined similarity, the account information and the password of the user to be authenticated may be extracted via the matched information feature sample.

Figure 7:
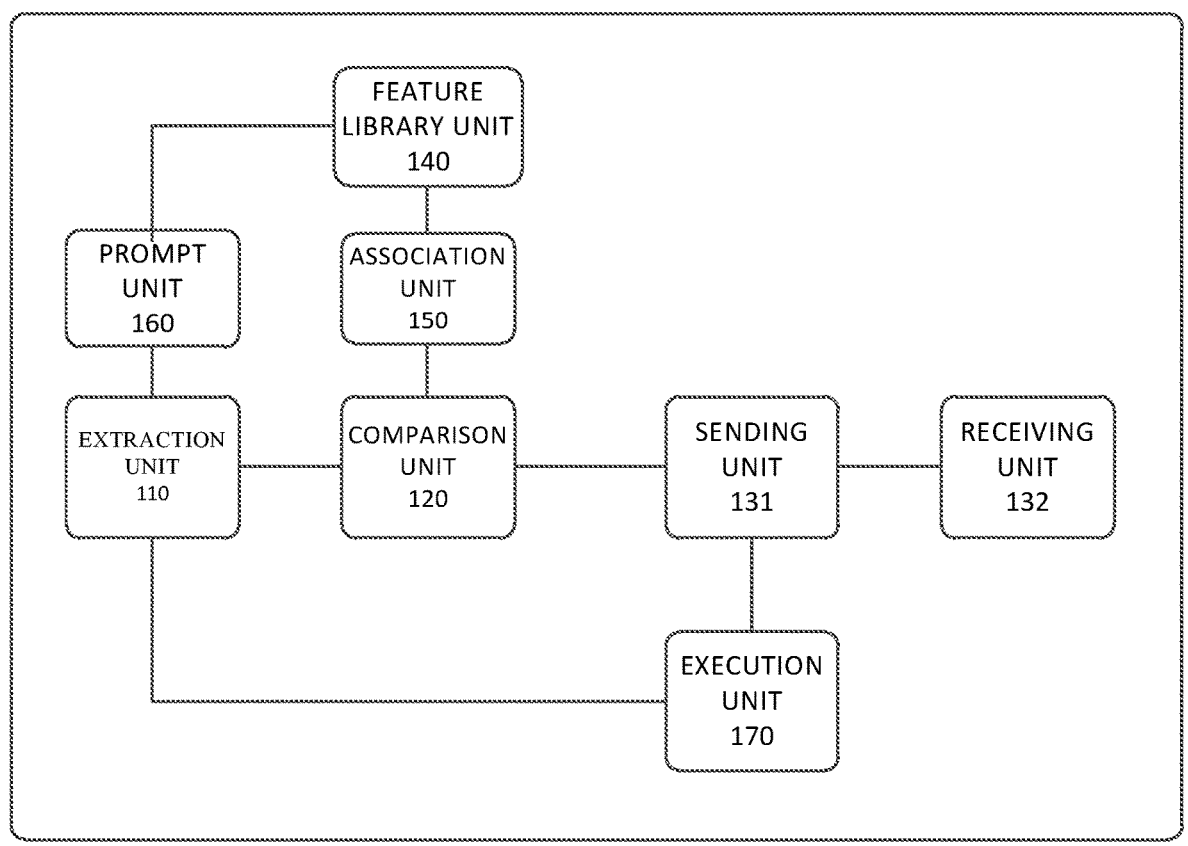
FIG. 7 illustrates an exemplary block diagram of an authentication device according to another embodiment of the present disclosure.

FIG. 7 illustrates an exemplary block diagram of an authentication device according to another embodiment of the present disclosure. As another embodiment of the present disclosure, the authentication device further comprises an execution unit 170. After an operation interface of an application corresponding to the cloud desktop is entered, the execution unit 170 is configured to determine an instruction corresponding to the signal feature of the user's brainwave signal according to the signal feature and control the application to execute the instruction. In some embodiments, when the user enters into the cloud desktop, the execution unit 170 may generate, according to the signal feature of the user's brainwave signal, an instruction for controlling an application, such as a page switch instruction, a file switch instruction, a play forward instruction, a play backward instruction, a file sharing instruction, and a location sharing instruction. The sending unit 131 is configured to send the instruction request to the cloud server, and the receiving unit 132 is configured to receive an operation of the cloud server in response to the request. In the embodiment, when the user enters into the operation interface of an application corresponding to the cloud desktop, he/she may control the operation of the application via his/her brainwave signal, thereby increasing convenience of use.

It should be noted that the correspondence relationship between the signal feature of the user's brainwave signal and the instruction may be established through repeated learning beforehand, which is similar to the process of associating the signal feature of the brainwave signal with the account information and the password as mentioned above. Moreover, the instruction corresponding to the signal feature of the brainwave signal may also be set according to the user's demands. A relatively accurate correspondence relationship therebetween may be established through repeated learning in advance.

Based on the same inventive concept, the embodiment of the present disclosure provides an authentication method for solving the same technical problem and achieving the same technical effect.

Figure 8:
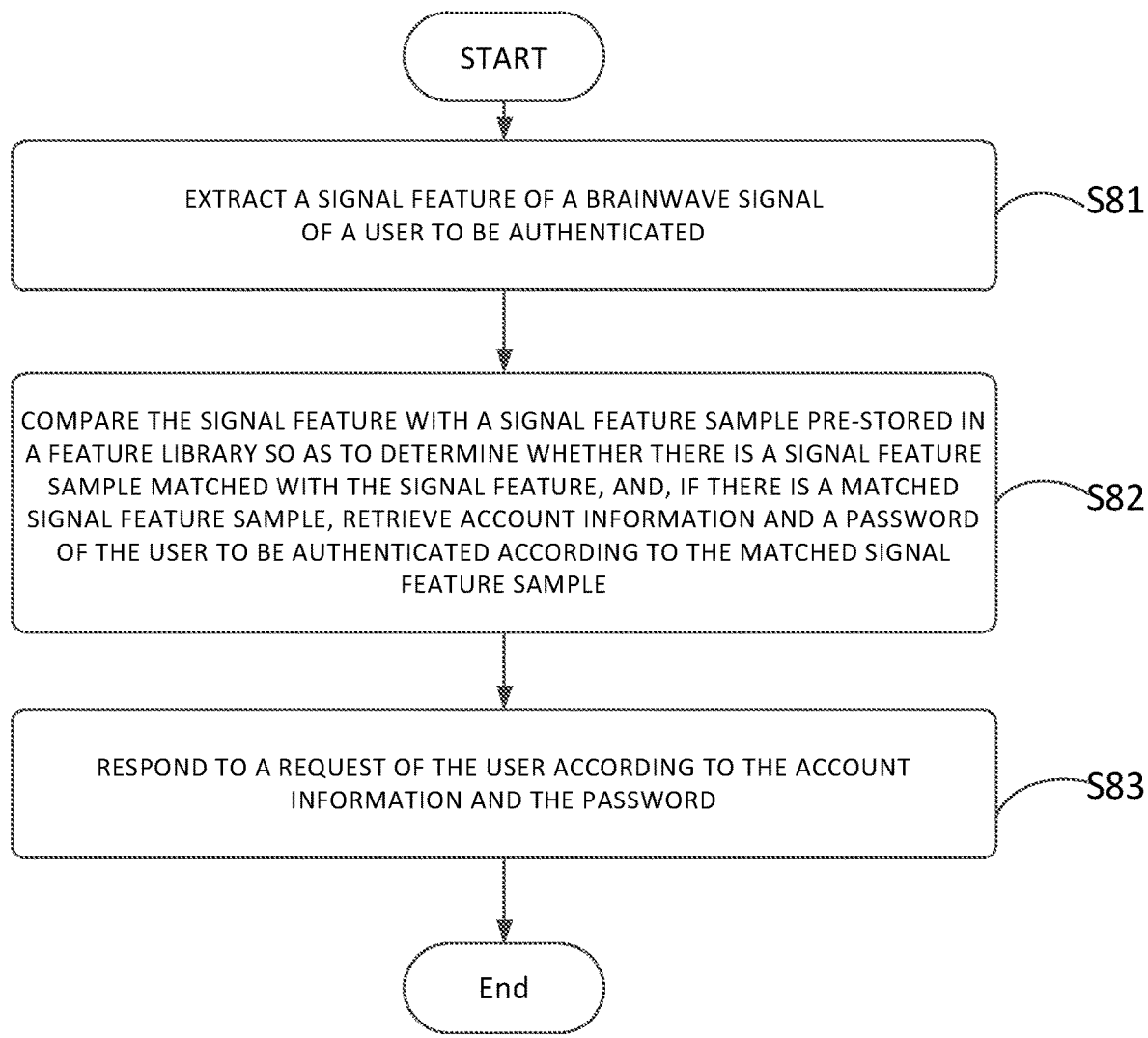
FIG. 8 is a flowchart showing an authentication method according to an embodiment of the present disclosure.

As shown in FIG. 8, as an embodiment of the present disclosure, the authentication method comprises:

Step S81: extracting a signal feature of a brainwave signal of a user to be authenticated;

Step S82: comparing the signal feature with a signal feature sample pre-stored in a feature library on an individual basis so as to determine whether there is a signal feature sample matched with the signal feature, and, if there is a matched signal feature sample, retrieving account information and a password of the user to be authenticated according to the matched signal feature sample; and Step S83: responding to a request of the user to be authenticated according to the account information and the password.

In this way, the authentication method provided by embodiments of the present disclosure may authenticate the identity of a user based on the user's brainwave signal feature, which improves the security and convenience of user identity authentication. Once the identity of the user is authenticated, the request of the user may be responded, thereby further improving user experience.

It should be noted that the request of the user to be authenticated may be, but not limited to, a login request, a payment request, a deletion request, a revocation request or an amendment request. Correspondingly, the password may be, but not limited to, a login password, a payment password, a deletion password, a revocation password or an amendment password. The login request may be, but not limited to, a request for logging into a user account on a browser (e.g., a request for logging in a cloud desktop) or a request for logging into a user account on an application.

Figure 9:
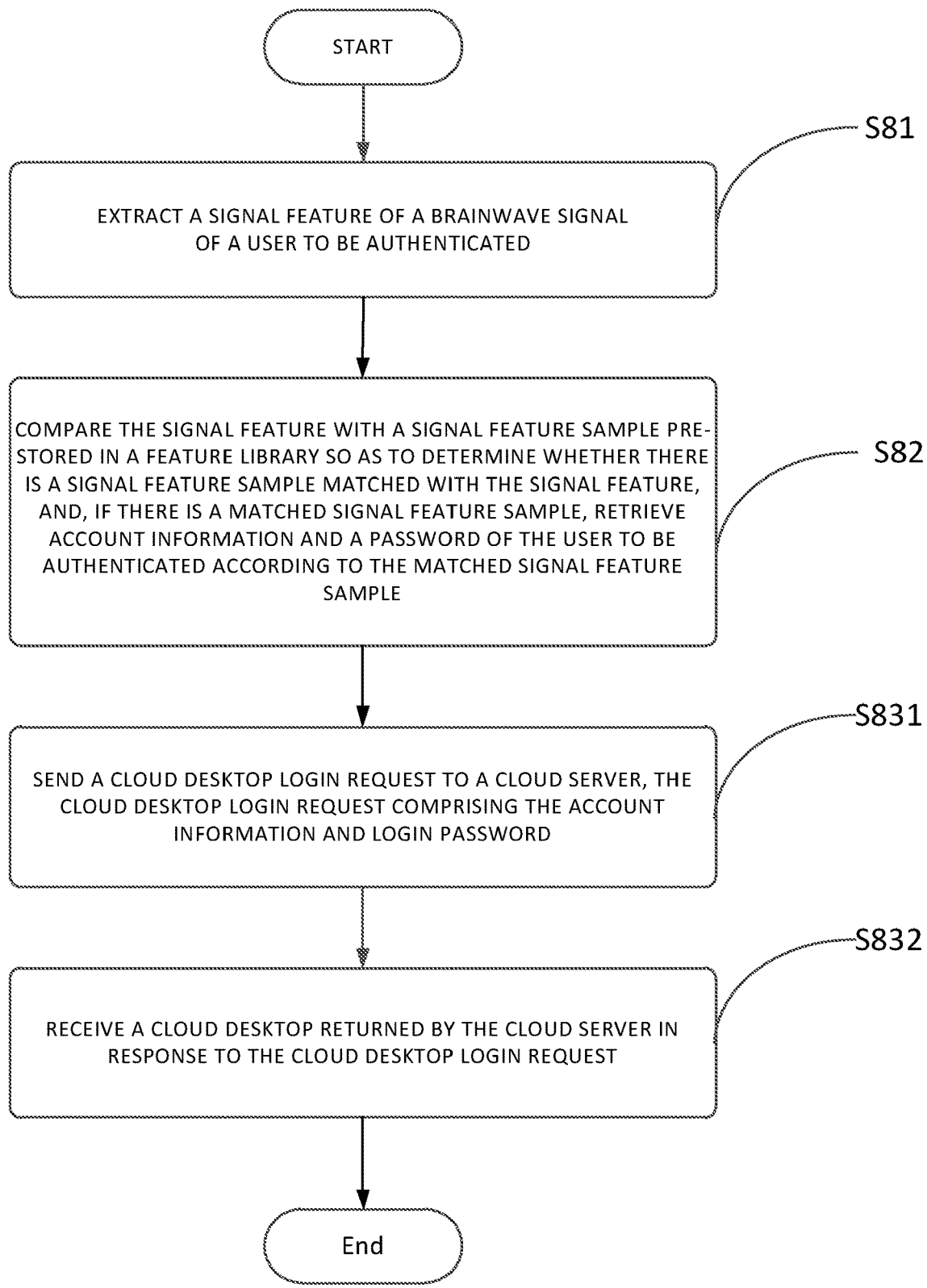
FIG. 9 is a flowchart showing an authentication method according to another embodiment of the present disclosure.

As shown in FIG. 9, as an embodiment of the present disclosure, the authentication method comprises:

Step S81: extracting a signal feature of a brainwave signal of a user to be authenticated;

Step S82: comparing the signal feature with a signal feature sample pre-stored in a feature library on an individual basis so as to determine whether there is a signal feature sample matched with the signal feature, and, if there is a matched signal feature sample, retrieving the account information and a login password of the user to be authenticated according to the matched signal feature sample;

Step S831: sending a cloud desktop login request to a cloud server, the cloud desktop login request comprising the account information and the login password; and Step S832: receiving a cloud desktop returned by the cloud server in response to the cloud desktop login request.

In this way, the authentication method provided by embodiments of the present disclosure may authenticate the identity of a user according to the user's brainwave signal feature. Once the authentication is passed, the cloud desktop login request may be directly sent to the cloud server and then the cloud desktop is logged in, which may enhance the security and convenience of logging into a cloud desktop.

The authentication method in the embodiment may be applied in a terminal, such as a cloud terminal, a PC, a hand-held device (e.g., a mobile phone or tablet) or a wearable device (e.g., a wrist band or head-mounted display device).

It shall be noted that the brainwave signal of the user may be collected by a brainwave detection device, such as a brainwave electrode cap. The authentication method authenticates an identity based on the brainwave signal collected by the brainwave detection device. Authentication via brainwave is more accurate than other manners of authentication. The brainwave signal features are characterized by hardness to replicate and uniqueness, which guarantees the security and accuracy of logging into a cloud desktop.

Figure 10:
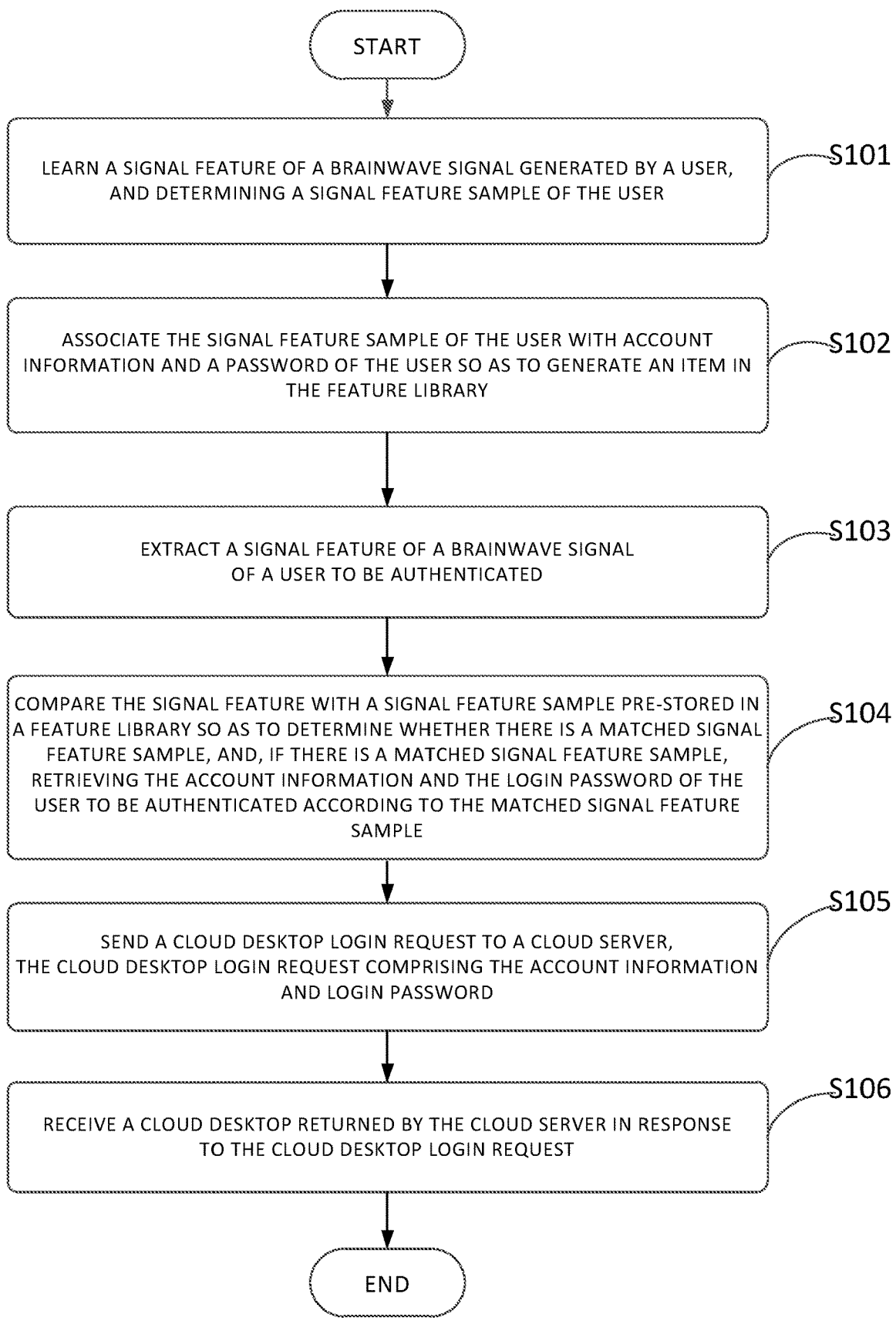
FIG. 10 is a flowchart showing an authentication method according to a further embodiment of the present disclosure.

As shown in FIG. 10, it is a flowchart showing an authentication method according to a further embodiment of the present disclosure. As a further embodiment of the present disclosure, the authentication method comprises:

Step S101: learning a signal feature of a brainwave signal generated by a user when conducting a specific thinking activity, and determining the signal feature sample of the user corresponding to the specific thinking activity;

Step S102: associating the determined signal feature sample of the user with account information and a login password of the user so as to generate an item in the feature library;

Step S103: extracting a signal feature of a brainwave signal of a user to be authenticated;

Step S104: comparing the signal feature with a signal feature sample pre-stored in a feature library on an individual basis so as to determine whether there is a signal feature sample matched with the signal feature, and, if there is a matched signal feature sample, retrieving the account information and the login password of the user to be authenticated according to the matched signal feature sample;

Step S105: sending a cloud desktop login request to a cloud server, the cloud desktop login request comprising the account information and the login password; and Step S106: receiving a cloud desktop returned by the cloud server in response to the cloud desktop login request.

The authentication method provided by the present disclosure determines signal feature samples corresponding to different users by respectively learning multiple times for each of the different users. It should be noted that accuracy of the signal feature samples may be enhanced by increasing the learning times. The signal feature sample of each user is associated with the account information and the password of the user in a one-to-one relationship. Thus, the user's identity may be accurately determined by the brainwave signal, thereby guaranteeing the security and accuracy of logging into the cloud desktop.

In some embodiments of the present disclosure, in order to further improve the authentication security and accuracy, the signal feature sample of each user may comprise a plurality of sub-signal feature samples, and each sub-signal feature sample corresponds to a signal feature of one category of thinking activities. Thus, after learning multiple times, it is possible to obtain the signal feature sample comprising a plurality of sub-signal feature samples corresponding to multiple categories of thinking activities, in such a way to enhance the accuracy, diversity and flexibility of identity authentication. Since the embodiments of the authentication method are substantially similar to those of the authentication device, they are described relatively simple. Please refer to the relevant embodiments of the device for details.

The Step S101 further comprises: prompting category information corresponding to the signal feature sample when the brainwave detection device collects the brainwave signal of a user. The Step S103 further comprises: prompting category information when the signal feature of the brainwave signal generated by the user is being learned. It should be noted that the category information prompted in the Step S101 may be identical to the category information prompted in the Step S103. In the Step S104, based on the same category of information, the signal feature is compared with the signal feature sample pre-stored in the feature library so as to enhance the accuracy of identity authentication.

As an embodiment of the present disclosure, in the Step S101, at least one of different categories of information corresponding to the signal feature sample may be prompted when the brainwave detection device is collecting the user's brainwave signal. As yet another embodiment of the present disclosure, in the Step S101, multiple different categories of information corresponding to the signal feature sample may also be prompted when the brainwave detection device is collecting the user's brainwave signal, in such a way to compare the signal feature corresponding to category information prompted with the sub-signal feature samples corresponding to the category information pre-stored in the feature library one by one. Since the embodiments of the authentication method are substantially similar to those of the authentication device, they are described relatively simple. Please refer to the relevant embodiments of the device for details.

Figure 11:
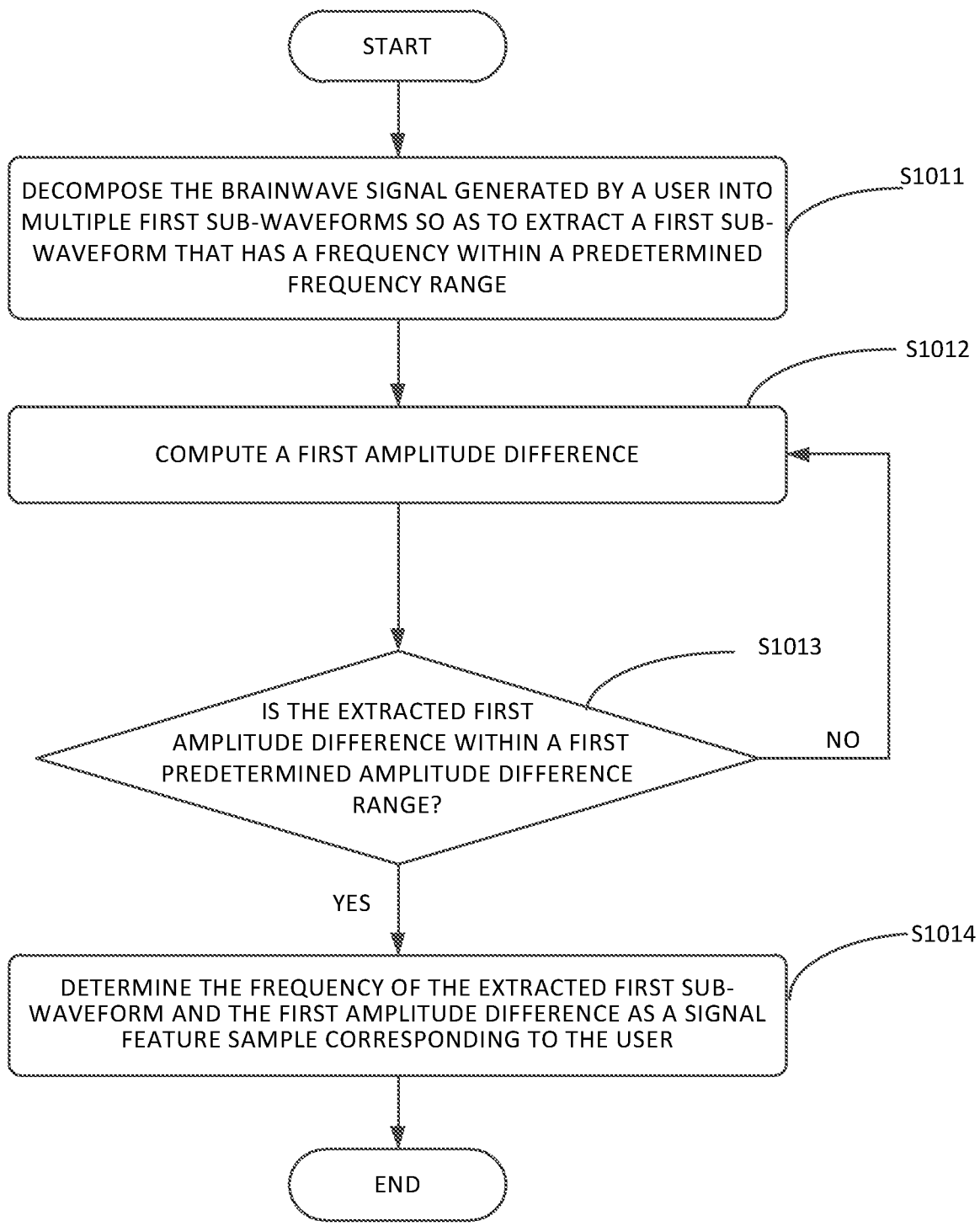
FIG. 11 is a flowchart showing steps of learning a feature signal according to an embodiment of the present disclosure.

As a further embodiment of the present disclosure, as shown in FIG. 11, the Step S101 may comprise:

Step S1011: decomposing the brainwave signal generated by a user into multiple first sub-waveforms so as to extract therefrom a first sub-waveform that has a frequency within a predetermined frequency range;

Step S1012: computing a first amplitude difference, which is the amplitude difference between the extracted first sub-waveform and a predetermined reference waveform;

Step S1013: determining whether the first amplitude difference is within a first predetermined amplitude difference range, and if yes, executing Step S1014, otherwise, executing Step S1012; and Step S1014: determining the frequency of the extracted first sub-waveform and the first amplitude difference as a signal feature sample corresponding to the user.

In this way, the authentication method provided by the embodiment of the present disclosure decomposes the brainwave signal into multiple first sub-waveforms, and computes the amplitude difference between the first sub-waveforms and a reference waveform, so as to obtain the signal feature sample for authenticating the user's identity according to the signal feature sample in the process of authentication.

As an embodiment of the present disclosure, the brainwave signal generated by a user may be decomposed into N (N being a natural number larger than zero) sections of first waveforms according to different time periods, and then M (M being a natural number larger than zero) sections of second waveforms are taken from the N sections. In such a way, the brainwave signal generated by the user is decomposed into multiple first sub-waveforms.

In the embodiment, the signal feature sample of the user's brainwave signal at different time instances are obtained according to whether the first amplitude difference is within the first predetermined amplitude difference range. The signal feature sample is a matrix-type signal feature $Im=[\varphi(ti), f]$, wherein $\varphi(ti)$ represents the amplitude difference between the user's brainwave signal and the reference waveform at the time ti, and f represents the frequency of the user's brainwave signal. Thus, the matrix comprises a plurality of feature elements with each representing the frequency of the user's brainwave signal at certain time and the amplitude difference between the user's brainwave signal and the reference waveform at certain time. It should be noted that the predetermined reference waveform may be a reference waveform self-defined by the user, so as to compute the amplitude difference with reference to it.

Figure 12:
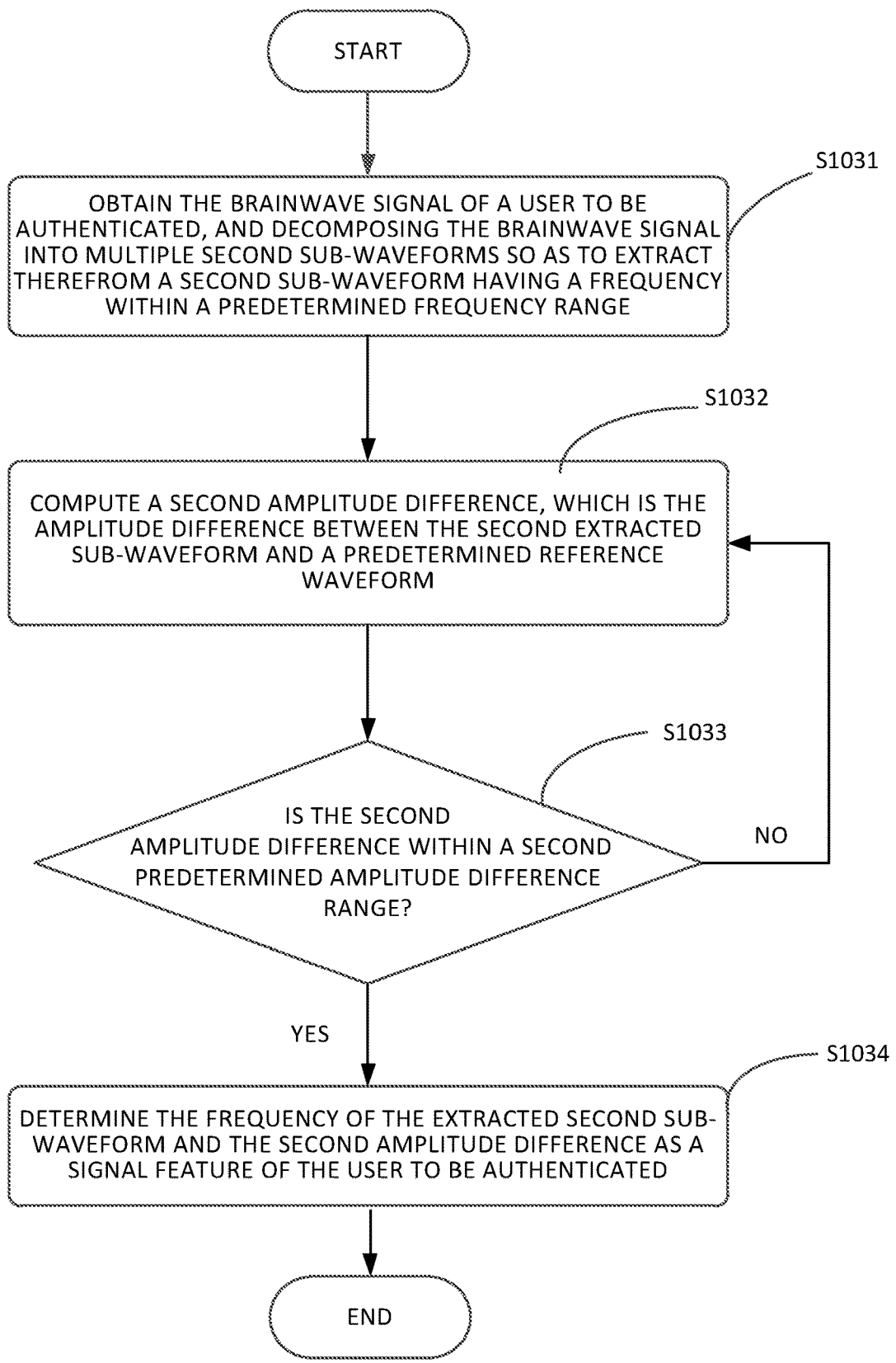
FIG. 12 is a flowchart showing steps of extracting a feature signal according to an embodiment of the present disclosure.

As a further embodiment of the present disclosure, as shown in FIG. 12, the Step S103 may comprise:

Step S1031: obtaining the brainwave signal of a user to be authenticated, and decomposing the brainwave signal of the user to be authenticated into multiple second sub-waveforms so as to extract therefrom a second sub-waveform that has a frequency within a predetermined frequency range;

Step S1032: computing a second amplitude difference, which is the amplitude difference between the extracted second sub-waveform and a predetermined reference waveform;

Step S1033: determining whether the second amplitude difference is within a second predetermined amplitude difference range, and if yes, executing Step S1034, otherwise, executing Step S1032; and Step S1034: determining the frequency of the extracted second sub-waveform and the second amplitude difference as the signal feature of the user to be authenticated.

In this way, the authentication method provided by the embodiment of the present disclosure decomposes the brainwave signal into multiple second sub-waveforms, and computes the amplitude difference between the multiple second sub-waveforms and respective reference waveforms, so as to obtain the signal feature of the user. The obtained signal feature is compare with the signal feature sample for authenticating the user's identity.

As an embodiment of the present disclosure, the brainwave signal of the user to be authenticated may be decomposed into R (R being a natural number larger than zero) sections of first waveforms according to different time periods, and each piece of first waveform may be decomposed into S (S being a natural number larger than zero) sections of second waveforms according to different time periods. In such a way, the brainwave signal of the user is decomposed into multiple first sub-waveforms. It should be pointed out that R may be identical to or different from N; S may be identical to or different from M; and the second predetermined amplitude may be identical to or different from the first predetermined amplitude. In the embodiment, the signal features of the brainwave signal of the user to be authenticated at different time instances are obtained according to whether the second amplitude difference is within the second predetermined amplitude difference range. The signal feature is a matrix-type signal feature $Pm=[\phi(ti), f]$, wherein $\phi(ti)$ represents the amplitude difference between the user's brainwave signal and the reference waveform at the time ti, and f represents the frequency of the user's brainwave signal. Thus, the matrix comprises a plurality of feature elements with each representing the frequency of the brainwave signal of the user to be authenticated at some time and the amplitude difference between the brainwave signal of the user to be authenticated and the reference waveform at some time.

Figure 13:
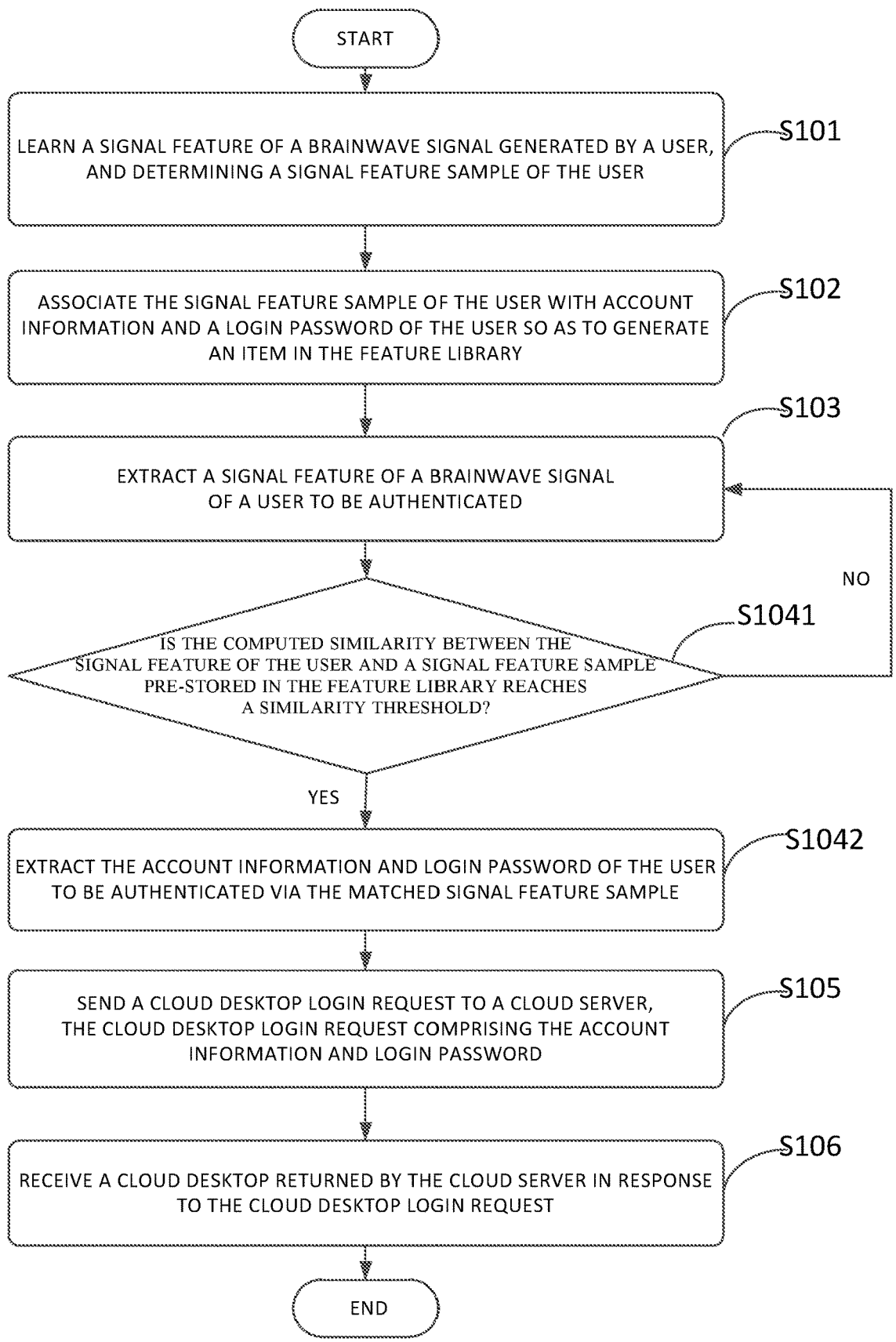
FIG. 13 is a flowchart showing an authentication method according to yet another embodiment of the present disclosure.

As yet another embodiment of the present disclosure, as shown in FIG. 13, the Step S104 comprises:

Step S1041: computing the similarity between the signal feature of the user and a signal feature sample pre-stored in the feature library so as to determine whether the similarity reaches a similarity threshold. If yes, executing Step S1042, otherwise, executing Step S103;

Step 1042: if the similarity reaches the similarity threshold, retrieving the account information and the password of the user via the matched signal feature sample.

In the embodiment, the similarity threshold may be pre-determined, such as 80%, 85% or 90%. When the similarity between the signal feature of the user to be authenticated and the signal feature sample pre-stored in the feature library exceeds the similarity threshold, it is deemed that they match with each other.

To be specific, the signal feature $Pm=[\phi(ti), f]$ of the user is compared with the signal feature sample $Im=[\phi(ti), f]$ pre-stored in the feature library on a feature element-by-feature element basis, so as to determine whether corresponding feature elements in the two matrixes are the same. A method for computing the similarity may be the number of feature elements identical to those of the signal feature of the user to be authenticated divided by the total number of feature elements in the signal feature sample. In certain exemplary embodiments, the signal feature $Pm=[\phi(ti), f]$ is compared with the signal feature sample $Im=[\phi(ti), f]$ pre-stored in the feature library on a parameter-by-parameter basis according to positions of parameters in the matrices so as to improve the accuracy of comparison. It should be noted that there are many ways to determine whether a pair of feature elements are the same. For example, this may be done by comparing the amplitude difference between feature elements. If the amplitude difference between the two feature elements is within a certain range, it may be determined that they are the same, though the present disclosure is not limited thereto.

As a further embodiment of the present disclosure, the Step S84 may comprise: computing the similarity between the signal feature of the user to be authenticated under some category information and the signal feature sample corresponding to the category information so as to determine whether the similarity reaches a predetermined similarity. If the similarity reaches the predetermined similarity, the account information and the password of the user to be authenticated may be extracted via the matched information feature sample.

As another embodiment of the present disclosure, the authentication method may also comprise: after an operation interface of an application corresponding to the cloud desktop is entered, determining an instruction corresponding to the signal feature of the user's brainwave signal according to the signal feature and controlling the application to execute the instruction. When the user enters into the cloud desktop, it is possible to generate, according to the signal feature of the user's brainwave signal, an instruction for controlling an application, such as a page switch instruction, a file switch instruction, a play forward instruction, a play backward instruction, a file sharing instruction, and a location sharing instruction, then to send a request of the instruction to the cloud server, and finally receive an operation of the cloud server performed in response to the request. In the embodiment, when the user enters into the operation interface of an application corresponding to the cloud desktop, the user may control the operation of the application via his/her brainwave signal, thereby increasing convenience of use.

It should be noted that the corresponding relationship between the signal feature of the user's brainwave signal and the instruction may be established through repeated learning beforehand, which is similar to the process of associating the signal feature of the brainwave signal with the account information and the password as mentioned above. Moreover, the instruction corresponding to the signal feature of the brainwave signal may also be set according to the user's demands. A relatively accurate corresponding relationship therebetween may be established through repeated learning in advance.

Since the embodiments of the authentication method are substantially similar to the embodiments of the device for authentication, they are described relatively simple. Please refer to the relevant embodiments of the device for details.

It may thus be seen that the authentication device and the authentication method provided by an embodiment of the present disclosure may authenticate identity according to a user's brainwave signal feature. When the authentication is passed, it is possible to directly send a cloud desktop login request to a cloud server and then log into the cloud desktop, which may enhance the security and convenience of logging into a cloud desktop. When the user enters into the operation interface of an application corresponding to the cloud desktop, the user may control the operation of the application via his/her brainwave signal, which increases convenience of use.

As used in this application, the terms "component," "unit," "system", "interface", and/or the like are generally intended to describe various devices associated with one or more operations. The "component," "unit," "system", etc., may be implemented using hardware elements, software elements, or a combination of both. Examples of hardware elements may include devices, components, processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The embodiments of the device as described above are merely exemplary, wherein units that are described as separate components may be or may not be physically apart, and components shown as a unit may be or may not be a physical unit, namely, they may be co-located, or distributed iii among a plurality of network units. Some or all modules may be selected according to actual requirements to realize the object of the solutions of the embodiments of the present disclosure. Those skilled in the art may understand and implement the present invention without undue experimentation.

From the description of the above embodiments, those skilled in the art may clearly know that various embodiments may be implemented by means of software and necessary general hardware platforms, or of course be implemented by hardware. Based on such an understanding, the technical solution may in essence or the part of the technical solution that contribute to the prior art may be embodied in the form of software products. The computer software product may be stored in a computer readable medium, such as ROM/RAM, a magnetic disk or a compact disk, and comprise a plurality of instructions to enable a computer device (which may be a PC, a server or a network device) to execute various embodiments or the method of some parts of the embodiments.

Those ordinarily skilled in the art may understand that the discussion of any above embodiment is merely exemplary, and not intended to imply that the scope of the present disclosure (including the claims) is limited to those examples. Under the idea of the present disclosure, the above embodiments or technical features in different embodiments may be combined, and there exist many other variations of the present disclosure in different embodiments, which will not be reiterated for the sake of brevity. Thus, within the spirit and principle of the present disclosure, any omission, amendment, alternative replacement or improvement should be included in the scope of protection of the present disclosure.

The invention claimed is:

1. A device for authentication, comprising:
    an extraction unit configured to extract a signal feature of a brainwave signal of a user to be authenticated;
    a comparison unit configured to compare the signal feature with one or more signal feature samples that are pre-stored in a feature library on an individual basis, wherein when one of the signal feature samples matches with the signal feature, the device for authentication retrieves account information and a password of the corresponding user according to the matched signal feature sample; and
    a response unit configured to respond to a request of the user corresponding to the account information and the password;
    wherein the extraction unit comprises:
        a first decomposition unit configured to obtain the brainwave signal of a user to be authenticated, decompose the brainwave signal of the user to be authenticated into multiple first sub-waveforms, and extract from them a first sub-waveform that has a frequency within a predetermined frequency range;
        a first computation unit configured to compute a first amplitude difference, wherein the first amplitude difference is the amplitude difference between the extracted first sub-waveform and a predetermined reference waveform; and
        a first determination unit configured to, when the first amplitude difference is within a first predetermined amplitude difference range, determine the frequency of the extracted first sub-waveform and the first amplitude difference as the signal feature of the user to be authenticated.

2. The device for authentication according to claim 1, wherein the password comprises a login password and the request comprises a cloud desktop login request, and the response unit comprises:
    a sending unit configured to send the cloud desktop login request to a cloud server, wherein the cloud desktop login request comprises the account information and the login password; and
    a receiving unit configured to receive a cloud desktop returned by the cloud server in response to the cloud desktop login request.

3. The device for authentication according to claim 1, further comprising:
    a feature library unit configured to determine the signal feature sample corresponding to a specific thinking activity of the user by learning the signal feature of the brainwave signal generated by the user when the user conducts the specific thinking activity; and
    an association unit configured to associate the determined signal feature sample with the account information and the password of the user so as to generate an item in the feature library.

4. The device for authentication according to claim 1, wherein the specific thinking activity comprises a thinking activity when the user is receiving a specific audiovisual content.

5. The device for authentication according to claim 4, wherein the feature library unit is configured to determine a plurality of corresponding sub-signal feature samples for a plurality of specific thinking activities of the user and wherein the association unit is configured to generate an item in the feature library for each of the plurality of determined sub-signal feature samples respectively.

6. The device for authentication according to claim 3, wherein the feature library unit comprises:
    a second decomposition unit configured to decompose the brainwave signal generated by the user into multiple second sub-waveforms and extract from them a second sub-waveform that has a frequency within the predetermined frequency range;
    a second computation unit configured to compute a second amplitude difference, wherein the second amplitude difference is the amplitude difference between the extracted second sub-waveform and the predetermined reference waveform; and
    a second determination unit configured to, when the second amplitude difference is within a second predetermined amplitude difference range, determine the frequency of the extracted second sub-waveform and the second amplitude difference as the signal feature sample corresponding to the user.

7. The device for authentication according to claim 1, wherein the comparison unit is further configured to compare the signal feature with a signal feature sample pre-stored in a feature library on an individual basis by: computing the similarity between the signal feature of the user to be authenticated and the signal feature sample so as to determine whether the similarity reaches a similarity threshold.

8. The device for authentication according to claim 7, wherein the comparison unit is further configured to compute the similarity according to a ratio of the number of feature elements identical to those of the signal feature of the user to be authenticated to the total number of feature elements in the signal feature sample.

9. The device for authentication according to claim 1, further comprising an execution unit, wherein the execution unit is configured to generate an instruction for controlling an application according to the signal feature of the brainwave signal of the user.

10. The device for authentication according to claim 9, wherein the instruction for controlling an application comprises at least one instruction selected from the group consisting of a page switch instruction, a file switch instruction, a play forward instruction, a play backward instruction, a file sharing instruction, and a location sharing instruction.

11. A method for authentication, comprising:
    extracting a signal feature of a brainwave signal of a user to be authenticated;
    comparing the signal feature with one or more signal feature samples that area pre-stored in a feature library on an individual basis, and, when one of the signal feature samples matches with the signal feature, retrieving account information and a password of the user according to the matched signal feature sample; and
    responding to a request of the user corresponding with the account information and the password;
    wherein said extracting a signal feature of a brainwave signal of a user to be authenticated comprises:
        obtaining the brainwave signal of the user to be authenticated, decomposing the brainwave signal of the user to be authenticated into multiple first sub-waveforms, and extracting from them a first sub-waveform that has a frequency within a predetermined frequency range;
        computing a first amplitude difference, wherein the first amplitude difference is the amplitude difference between the extracted first sub-waveform and a predetermined reference waveform; and determining the frequency of the extracted first sub-waveform and the first amplitude difference as the signal feature of the user to be authenticated when the first amplitude difference is within a first predetermined amplitude difference range.

12. The method for authentication according to claim 11, wherein the password comprises a login password and the request comprises a cloud desktop login request, and said responding to the request of the user corresponding with the account information and the password comprises:
    sending the cloud desktop login request to a cloud server, wherein the cloud desktop login request comprises the account information and the login password; and
    receiving a cloud desktop returned by the cloud server in response to the cloud desktop login request.

13. The method for authentication according to claim 11, wherein before extracting a signal feature of a brainwave signal of a user to be authenticated, the method further comprises:
    determining a signal feature sample corresponding to a specific thinking activity for the user by learning the signal feature of the brainwave signal generated by the user when the user conducts the specific thinking activity; and
    associating the determined signal feature sample with the account information and the password of the user so as to generate an item in the feature library.

14. The method for authentication according to claim 13, wherein the specific thinking activity comprises a thinking activity when the user is receiving a specific audiovisual content.

15. The method for authentication according to claim 14, wherein said determining the signal feature sample corresponding to a specific thinking activity for the user comprises determining a plurality of corresponding sub-signal feature samples for a plurality of specific thinking activities of the user; and
    said generating an item in the feature library comprises generating an item in the feature library for each of the plurality of determined sub-signal feature samples, respectively.

16. The method for authentication according to claim 13, wherein said determining the signal feature sample corresponding to the user comprises:
    decomposing the brainwave signal generated by the user into multiple second sub-waveforms and extracting from them a second sub-waveform that has a frequency within the predetermined frequency range;
    computing a second amplitude difference, wherein the second amplitude difference is the amplitude difference between the extracted second sub-waveform and the predetermined reference waveform; and
    when the second amplitude difference is within a second predetermined amplitude difference range, determining the frequency of the extracted first sub-waveform and the second amplitude difference as the signal feature sample corresponding to the user.

17. A system for authentication, comprising one or more processors; and a memory coupled to the one or more processors, the memory comprising instructions that, when executed by the one or more processors, cause the system to:
    extract a signal feature of a brainwave signal of a user to be authenticated;
    compare the signal feature with one or more signal feature samples that are pre-stored in a feature library on an individual basis, and, when one of the one or more signal feature samples matches with the signal feature, retrieving account information and a password of the user according to the matched signal feature sample; and
    respond to a request of the user corresponding with the account information and the password;
    wherein the system is caused to extract the signal feature of the brainwave signal of the user to be authenticated by:
        obtaining the brainwave signal of the user to be authenticated, decomposing the brainwave signal of the user to be authenticated into multiple first sub-waveforms, and extracting from them a first sub-waveform that has a frequency within a predetermined frequency range;
        computing a first amplitude difference, wherein the first amplitude difference is the amplitude difference between the extracted first sub-waveform and a predetermined reference waveform; and
        determining the frequency of the extracted first sub-waveform and the first amplitude difference as the signal feature of the user to be authenticated when the first amplitude difference is within a first predetermined amplitude difference range.

18. A transitory computer readable storage medium storing instructions that, when executed by at least one central processor unit of a computing device, cause the computing device to carry out the method according to claim 11.

* * * * *